United States Patent
Ochiai et al.

(10) Patent No.: US 8,609,735 B2
(45) Date of Patent: Dec. 17, 2013

(54) RAPID-ACTING, BLOOD-ARGININE-LEVEL-INCREASABLE ORAL PREPARATION COMPRISING CITRULLINE AND ARGININE

(75) Inventors: Masayuki Ochiai, Tokyo (JP); Koji Morishita, Ibaraki (JP); Toshio Hayashi, Aichi (JP)

(73) Assignees: Kyowa Hakko Bio Co., Ltd., Tokyo (JP); National University Corporation Nagoya University, Nagoya (JP)

( * ) Notice: Subject to any disclaimer, the term of this patent is extended or adjusted under 35 U.S.C. 154(b) by 337 days.

(21) Appl. No.: 12/682,483

(22) PCT Filed: Oct. 10, 2008

(86) PCT No.: PCT/JP2008/068505
§ 371 (c)(1),
(2), (4) Date: Jul. 9, 2010

(87) PCT Pub. No.: WO2009/048148
PCT Pub. Date: Apr. 16, 2009

(65) Prior Publication Data
US 2010/0292332 A1  Nov. 18, 2010

(30) Foreign Application Priority Data
Oct. 10, 2007 (JP) .................................. 2007-264090

(51) Int. Cl.
*A61K 31/155* (2006.01)
*A61K 36/00* (2006.01)

(52) U.S. Cl.
USPC ............................ 514/633; 514/634; 424/777

(58) Field of Classification Search
USPC ........................... 514/634, 633; 424/725, 777
See application file for complete search history.

(56) References Cited

FOREIGN PATENT DOCUMENTS

WO   WO 95/06467 A1   3/1995
WO   WO 2005/107735 A2   11/2005

OTHER PUBLICATIONS

Barbul et al., *Surgery*, 108(2): 331-337 (1990).
Bessman et al., *The New England Journal of Medicine*, 256(20): 941-943 (1957).
Blum et al., *J. Lab. Clin. Med.*, 135(3): 231-237 (2000).
Du Ruisseau et al., *Archives of Biochemistry and Biophysics*, 64: 355-367 (1956).
Chen et al., *BJU International*, 83: 269-273 (1999).
Chen et al., *Laboratory Investigation*, 68(2): 174-184 (1993).
Cui et al., *Nutrition*, 15(7/8): 563-569 (1999).
Curis et al., *Amino Acids*, 29: 177-205 (2005).
Floyd et al., *Journal of Clinical Investigation*, 45(9): 1487-1502 (1966).
Hambrecht et al., *Journal of the American College of Cardiology*, 35(3): 706-713 (2000).
Hayashi et al., *Proc. Natl. Acad. Sci.*, 102(38): 13681-13686 (2005).
Osowska et al., *Gut*, 53: 1781-1786 (2004).

*Primary Examiner* — Kevin E Weddington
(74) *Attorney, Agent, or Firm* — Leydig, Voit & Mayer, Ltd.

(57) ABSTRACT

The present invention provides a rapid-acting, blood arginine level-increasing oral preparation containing citrulline or a salt thereof and arginine or a salt thereof as active ingredients. The rapid-acting, blood arginine level-increasing oral preparation of the present invention can rapidly and effectively increase blood arginine level after ingestion, and can rapidly provide an arginine ingestion effect.

6 Claims, 3 Drawing Sheets

RAPID-ACTING, BLOOD-ARGININE-LEVEL-INCREASABLE ORAL PREPARATION COMPRISING CITRULLINE AND ARGININE

TECHNICAL FIELD

The present invention relates to a rapid-acting, blood arginine level-increasing oral preparation comprising citrulline or a salt thereof and arginine or a salt thereof, which is capable of increasing the blood arginine level rapidly and effectively.

BACKGROUND ART

Arginine is an amino acid to be a direct substrate of nitric oxide (NO) synthase. Moreover, it is an intermediate in the urea cycle in the liver, and plays an important role in detoxication of ammonia produced in the body. As its physiological actions, vasodilation due to oral ingestion of arginine (non-patent document 1), suppression of blood pressure increase (non-patent document 2), improvement of sexual function (non-patent document 3) and the like have been reported.

In addition, arginine is known to have a growth hormone secretory action (non-patent document 4). Since the growth hormone has an action to promote protein synthesis, sugar metabolism, lipid metabolism and the like, ingestion of arginine is expected to provide a muscle synthesis action and a wound healing action. In addition, there are many effects exerted by oral ingestion by animals and human, such as ammonia detoxication (non-patent document 5), immuno-stimulation (non-patent document 6), insulin secretion (non-patent document 7), polyamine synthesis action (non-patent document 8) and the like.

Thus, enhancement of the arginine level of the body is considered to be useful for maintenance of health and improvement of disease condition. In fact, arginine is ingested in the form of pharmaceutical products, functional foods and the like with an expectation of such effects.

On the other hand, citrulline is not used as a starting material for the synthesis of protein in the body, and is one kind of amino acid present in a free form. In the body, citrulline plays an important role as an arginine precursor for arginine biosynthesis or a constituent factor of NO cycle relating to NO supply.

It is known that orally ingested citrulline is mostly converted to arginine in the kidney and arginine is efficiently supplied systemically (non-patent document 9). To increase blood arginine level, ingestion of citrulline is reported to be more effective than ingestion of arginine itself (non-patent document 10). In addition, it is reported that ingestion of citrulline and arginine in combination enhances NO production and strengthen an anti-arteriosclerosis action, rather than individual ingestion of each (non-patent document 11). However, these are effects provided by long-term ingestion.

On the other hand, among the effects expected to result in prevention or improvement by the enhancement of the blood arginine level, appearance of effect in a short time after ingestion is desired in temporary symptoms caused by decreased blood flow, such as sensitivity to coldness, swelling, stiff shoulders, erectile dysfunction and the like, muscle fatigue due to accumulation of ammonia after exercise and the like. However, an oral preparation that rapidly and effectively increases blood arginine level after ingestion is not known.

non-patent document 1: "Journal of the American College of Cardiology", 2000, vol. 35, p. 706-713
non-patent document 2: "Laboratory Investigation", 1993, vol. 68, p. 174-184
non-patent document 3: "BJU International", 1999, vol. 83, p. 269-273
non-patent document 4: "Journal of Laboratory & Clinical Medicine", 2000, vol. 135, p. 231-237
non-patent document 5: "New England Journal of Medicine", 1957, vol. 256, p. 941-943
non-patent document 6: "Surgery", 1990, vol. 108, p. 331-336, 336-337
non-patent document 7: "Journal of Clinical Investigation", 1966, vol. 45, p. 1487-1502
non-patent document 8: "Nutrition", 1999, vol. 15, p. 563-569
non-patent document 9: "Amino acids", 2005, vol. 29, p. 177-205
non-patent document 10 "Gut", 2004, vol. 53, p. 1781-1786
non-patent document 11: "PNAS" 2005, vol. 102, p. 13681-13686

DISCLOSURE OF THE INVENTION

Problems to be Solved by the Invention

An object of the present invention is to provide an oral preparation and method for rapidly and effectively increasing blood arginine level after ingestion, and provide an oral preparation and method rapidly affording an ingestion effect of arginine.

Means of Solving the Problems

The present inventors have conducted intensive studies in an attempt to solve the above-mentioned problems and found that an oral preparation comprising citrulline or a salt thereof and arginine or a salt thereof as active ingredients can increase blood arginine level rapidly after oral ingestion, which resulted in the completion of the present invention.

Accordingly, the present invention relates to the following [1]-[18].

[1] A rapid-acting, blood arginine level-increasing oral preparation comprising citrulline or a salt thereof and arginine or a salt thereof as active ingredients.
[2] A rapid-acting, blood arginine level-increasing oral preparation in the form of a kit or set, comprising an oral preparation comprising citrulline or a salt thereof as an active ingredient and an oral preparation comprising arginine or a salt thereof as an active ingredient.
[3] The oral preparation of the above-mentioned [1] or [2] for promoting the blood flow.
[4] The oral preparation of the above-mentioned [1] or [2], which is for the prevention or improvement of a symptom caused by decreased blood flow.
[5] The oral preparation of the above-mentioned [4], wherein the symptom caused by decreased blood flow is at least one symptom selected from stiff shoulders, sensitivity to cold, swelling and erectile dysfunction.
[6] The oral preparation of the above-mentioned [1] or [2], which is for suppressing an increase in blood ammonia level.
[7] The oral preparation of the above-mentioned [1] or [2], which is for the prevention or improvement of a symptom caused by an increase in blood ammonia level.
[8] The oral preparation of the above-mentioned [7], wherein the symptom caused by an increase in blood ammonia level is muscle fatigue or feeling of fatigue after exercise.
[9] Use of citrulline or a salt thereof and arginine or a salt thereof for the production of a rapid-acting, blood arginine level-increasing oral preparation.

[10] Use of citrulline or a salt thereof and arginine or a salt thereof, for the production of a rapid-acting oral preparation for promoting blood flow.

[11] Use of citrulline or a salt thereof and arginine or a salt thereof for the production of a rapid-acting oral preparation for the prevention or improvement of a symptom caused by decreased blood flow.

[12] Use of citrulline or a salt thereof and arginine or a salt thereof for the production of a rapid-acting oral preparation for suppressing an increase in blood-ammonia level.

[13] Use of citrulline or a salt thereof and arginine or a salt thereof for the production of a rapid-acting oral preparation for the prevention or improvement of a symptom caused by increased blood ammonia level.

[14] A method of rapid-actingly increasing blood arginine level, comprising a step of administering citrulline or a salt thereof and arginine or a salt thereof to a test subject in need of rapid-acting increase in the blood arginine level in amounts sufficient to rapid-actingly increase the arginine blood level of the test subject.

[15] A method of rapid-actingly increasing blood flow, comprising a step of administering citrulline or a salt thereof and arginine or a salt thereof to a test subject in need of rapid-acting increase in the blood flow in amounts sufficient to increase the blood flow of the test subject.

[16] A method of rapid-acting preventing or improving a symptom caused by decreased blood flow, comprising a step of administering citrulline or a salt thereof and arginine or a salt thereof to a test subject in need of rapid-acting prevention or improvement of the symptom in amounts sufficient to prevent or improve the symptom of the test subject.

[17] A method of rapid-actingly suppressing an increase in blood ammonia level, comprising a step of administering citrulline or a salt thereof and arginine or a salt thereof to a test subject in need of rapid-acting suppression of the increase in blood ammonia level in amounts sufficient to suppress the increase in the blood ammonia level of the test subject.

[18] A method of rapid-actingly preventing or improving a symptom caused by increased blood ammonia level, comprising a step of administering citrulline or a salt thereof and arginine or a salt thereof to a test subject in need of rapid-acting prevention or improvement of the symptom in amounts sufficient to prevent or improve the symptom of the test subject.

Effect of the Invention

Since the present invention can rapidly and effectively increase arginine blood level, various symptoms caused by decreased blood flow or increased blood ammonia level can be improved in a short time. Moreover, since the oral preparation of the present invention is highly safe, development of the symptom can be effectively prevented by ingesting the preparation not only before predictable development of the symptom but routinely.

BEST MODE FOR CARRYING OUT THE INVENTION

Figure 1:
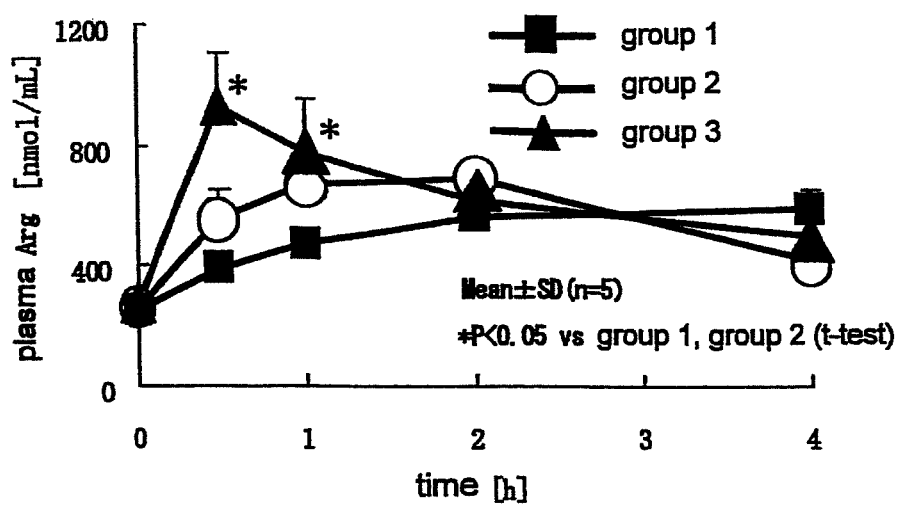
FIG. 1 shows time-course changes in plasma arginine level (unit: nmol/mL) after oral administration.

The present invention relates to a rapid-acting, blood arginine level-increasing oral preparation (sometimes to be referred to as the oral preparation of the present invention) comprising citrulline or a salt thereof and arginine or a salt thereof as active ingredients. In the present invention, the "rapid-acting, blood arginine level-increasing oral preparation" is an oral preparation that rapidly increases blood arginine level by oral ingestion by or oral administration to human or animals other than human.

In other words, the oral preparation of the present invention can rapidly increase blood arginine level in the body. In the present invention, "increase blood arginine level" means increasing the area under the blood concentration-time curve (AUC) of arginine as compared to single administration of each of arginine or a salt thereof or citrulline or a salt thereof. Here, the "area under the blood concentration-time curve (AUC)" refers to the area enclosed by the curve (blood drug concentration-time curve) and the horizontal axis (temporal axis) in a graph showing the time-course progress of blood concentration of a drug and the like, and is a useful index of drug amount in the body and the like.

While the citrulline and arginine to be used in the present invention may be in any of the L-form, D-form and DL-form, L-form is preferable.

In addition, citrulline and arginine and salts thereof to be used in the present invention can be obtained by a method including isolating and purifying them from animals and plants containing a large amount thereof, a method including chemical synthesis, a method including fermentation production and the like. Moreover, commercially available products thereof can also be purchased from, for example, Sigma-Aldrich and the like.

Examples of the salts of citrulline and arginine to be used in the present invention include acid addition salts, metal salts, ammonium salts, organic amine addition salts, amino acid addition salts and the like.

Examples of the above-mentioned acid addition salt include inorganic acid salts such as hydrochloride, sulfate, nitrate, phosphate and the like, organic salts such as acetate, maleate, fumarate, citrate, malate, lactate, α-ketoglutarate, gluconate, caprylate and the like.

Examples of the above-mentioned metal salt include alkali metal salts such as sodium salt, potassium salt and the like, alkaline earth metal salts such as magnesium salt, calcium salt and the like, aluminum salt, zinc salt and the like. % Examples of the above-mentioned ammonium salt include salts of ammonium, tetramethylammonium and the like.

Examples of the above-mentioned organic amine addition salt include salts of morpholine, piperidine and the like.

Examples of the above-mentioned amino acid addition salt include salts of glycine, phenylalanine, lysine, aspartic acid, glutamic acid and the like.

In the present invention, as a salt of citrulline, malate is preferable. In addition, as a salt of arginine, hydrochloride and aspartate are preferable.

As the oral preparation of the present invention, citrulline or a salt thereof and arginine or a salt thereof can be directly ingested or administered. It is generally desirable to provide them in the form of various preparations.

The above-mentioned preparation of the present invention contains citrulline or a salt thereof and arginine or a salt thereof as active ingredients, and may further contain any active ingredient. Such preparation is produced by mixing the active ingredients with one or more kinds of pharmacologically acceptable carriers, and according to any method well-known in the technical field of pharmaceuticals.

Examples of the dosage form of the oral preparation of the present invention include tablet, powder, granule, emulsion, syrup, capsule and the like, with preference given to tablet and granule. When the oral preparation of the present invention is formulated, for example, additives such as excipient, binder, disintegrant, lubricant, dispersing agent, suspending agent, emulsifier, diluent, buffer, antioxidant, bacteria suppressive agent, corrigent, flavor, colorant and the like can be used.

For example, when the dosage form of the oral preparation is tablet, powder, granule and the like, saccharides such as lactose, sucrose, glucose, saccharose, mannitol, sorbitol and the like, starch such as potato, wheat, corn and the like, inorganic material such as calcium carbonate, calcium sulfate, sodium hydrogen carbonate, sodium chloride and the like, excipient such as plant powder (Glycyrrhiza uralensis, Gentiana lutea powder etc.) and the like, disintegrant such as starch, agar, gelatin powder, crystalline cellulose, carmellose sodium, carmellose calcium, calcium carbonate, sodium hydrogen carbonate, sodium alginate and the like, lubricant such as magnesium stearate, talc, hydrogenated vegetable oil, macrogol, silicon oil and the like, binder such as polyvinyl alcohol, hydroxypropylcellulose, methylcellulose, ethylcellulose, carmellose, gelatin, starch glue solution and the like, surfactant such as fatty acid ester and the like, plasticizer such as glycerol etc. and the like can be added for formulation of the preparation.

When the dosage form of the oral preparation is a liquid preparation such as syrup and the like, water, saccharides such as saccharose, sorbitol, fructose and the like, glycols such as polyethylene glycol, propylene glycol and the like, oils such as sesame oil, olive oil, soybean oil and the like, preservative such as p-hydroxybenzoic acid esters and the like, flavors such as strawberry flavor, peppermint etc. and the like can be added for formulation of the preparation.

In the oral preparation of the present invention, moreover, citrulline or a salt thereof and arginine or a salt thereof may be contained in the same oral preparation, or each material may be separately formulated into a preparation, and they may be combined and used as a rapid-acting, blood arginine level-increasing oral preparation in the form of a kit or set (hereinafter sometimes to be simply referred to as a kit etc.).

Respective oral preparations contained in the above-mentioned kit etc. may be in any form as long as they are individually present. For example, respective oral preparations may be in different dosage forms, or may be individually packaged, or may be enclosed in the same container.

The oral preparation of the present invention may be used as is or as foods or drinks such as health food, functional food, dietary supplement, food for specified health uses and the like in the form of, for example, powder food, sheet-like food, bottled food, canned food, retort food, capsule food, tablet-like food, fluid diet, drinkable preparation and the like by adding additive to be generally used for food or drink. Examples of the above-mentioned additive include sweetener, colorant, preservative, thickening stabilizer, antioxidant, color developing agent, brightener, fungicide, gum base, bittering agent, enzyme, glossing agent, acidulant, seasoning, emulsifier, toughening agent, agent for production, flavor, spice extract and the like. In addition, when the food or drink are health food, functional food, dietary supplement, food for specified health uses and the like, a form wherein citrulline or a salt thereof and arginine or a salt thereof for unit ingestion is packed or a drink containing citrulline or a salt thereof and arginine or a salt thereof suspended or dissolved therein is filled in a bottle and the like for a single consumption and the like can be mentioned.

The contents of citrulline or a salt thereof and arginine or a salt thereof in the oral preparation of the present invention are appropriately determined depending on the kind of preparation, effects expected by the administration or ingestion of the preparation and the like. The total amount of citrulline or a salt thereof and arginine or a salt thereof is generally 0.1-100 wt %, preferably 0.5-80 wt %, particularly preferably 1-70 wt %, based on free citrulline and arginine. In addition, the composition ratio in weight of citrulline or a salt thereof and arginine or a salt thereof in the oral preparation of the present invention is 1:20-20:1, preferably 1:5-5:1, particularly preferably 1:2-2:1, based on free citrulline and arginine.

While the dose and administration frequency of the oral preparation of the present invention for ingestion or administration vary depending on the administration form, the age, body weight and the like of the subject of administration, the total amount of citrulline or a salt thereof and arginine or a salt thereof is generally 50 mg-30 g, preferably 100 mg-10 g, particularly preferably 200 mg-3 g, for an adult per day based on free citrulline and arginine, which is generally administered in one to several portions a day. Moreover, while the dosing period is not particularly limited, it is generally 1 day-1 year, preferably 1 week-3 months.

The oral preparation of the present invention can be used not only for human but also for animals other than human (hereinafter to be abbreviated as non-human animal). Examples of the non-human animal include mammals, birds, reptiles, amphibians, fish and the like, with preference given to mammalian non-human animals.

While the dose for administration to a non-human animal varies depending on the age and species of the animal, the kind or severity of symptom, and the like, the total amount of citrulline or a salt thereof and arginine or a salt thereof is generally 1-600 mg, preferably 2-200 mg, more preferably 4-60 mg, per kg/day based on free citrulline and arginine, which is generally administered in one to several portions a day. Moreover, while the dosing period is not particularly limited, it is generally 1 day-1 year, preferably 1 week-3 months.

The oral preparation of the present invention can be used for increasing blood flow. In addition, the oral preparation of the present invention can be used for the prevention or improvement of symptoms caused by decreased blood flow. Examples of the symptoms caused by decreased blood flow include stiff shoulders, sensitivity to cold, swelling, erectile dysfunction and the like.

In addition, the oral preparation of the present invention can be used for suppressing an increase in blood ammonia level. Moreover, the oral preparation of the present invention can be used for the prevention or improvement of symptoms caused by increased blood ammonia level. Examples of the symptom caused by increased blood ammonia level include muscle fatigue and feeling of fatigue after exercise and the like. Since the oral preparation of the present invention is rapid-acting, muscle fatigue, feeling of fatigue and the like can be effectively prevented or rapidly recovered by ingestion before and after exercise.

Furthermore, in the present invention, citrulline or a salt thereof and arginine or a salt thereof are used for the production of a rapid-acting, blood arginine level-increasing oral preparation. A rapid-acting, blood arginine level-increasing oral preparation can be produced as an oral preparation for increasing blood flow or an oral preparation for the prevention or improvement of symptoms caused by decreased blood flow, or an oral preparation for suppressing an increase in blood ammonia level or an oral preparation for the prevention or improvement of symptoms caused by increased blood ammonia level.

Moreover, the present invention encompasses a method of rapid-actingly increasing blood arginine level. The method of the present invention includes a step of administering citrulline or a salt thereof and arginine or a salt thereof to a test subject in need of rapid-acting increase in the blood arginine level in amounts sufficient to rapid-actingly increase the arginine blood level of the test subject. The method includes, as a method of rapid-actingly increasing blood flow or a method of rapid-actingly preventing or improving a symptom caused by decreased blood flow, a step of administering citrulline or a salt thereof and arginine or a salt thereof to a test subject in need of increased blood flow or prevention or improvement of the symptom, in amounts sufficient to rapid-actingly increase the blood flow or rapid-actingly prevent or improve the symptom of the test subject. Furthermore, the method includes a method of rapid-actingly suppressing an increase in blood ammonia level or a method of rapid-actingly preventing or improving a symptom caused by increased blood ammonia level, which comprises a step of administering citrulline or a salt thereof and arginine or a salt thereof to a test subject in need of suppression of the increase in blood ammonia level or prevention or improvement of the symptom, in amounts sufficient to rapid-actingly suppress the increase in the blood ammonia level or rapid-actingly prevent or improve the symptom of the test subject.

Specific embodiments, the amounts to be used and the like of citrulline or a salt thereof and arginine or a salt thereof used for the above-mentioned production etc. of a rapid-acting, blood arginine level-increasing oral preparation, and the above-mentioned method etc. of rapid-actingly increasing arginine blood level and the like are as mentioned above. In the above, moreover, the "test subject" includes human and non-human animals.

EXAMPLES

The present invention is explained in more detail in the following by referring to Examples.

First, experimental examples are shown, in which the effects of a rapid-acting, blood arginine level-increasing oral preparation comprising L-citrulline and L-arginine were studied.

Experimental Example 1

A catheter was indwelled in the jugular vein of each of fifteen 9-week-old male SD rats (Japan slc, Inc.). The rats were preliminarily bred for 3 days and divided into 3 groups. Under non-fasting conditions, L-citrulline and L-arginine were orally administered to the rats of group 1 and group 2, respectively, by a sonde to achieve 2.85 mmol/kg per rat for both (499.3 mg/kg and 496.5 mg/kg, respectively). Moreover, L-citrulline and L-arginine were orally administered to the rats of group 3 by a sonde to achieve 1.43 mmol/kg per rat (250.5 mg/kg and 249.1 mg/kg, respectively).

The blood was collected from the jugular vein before administration, and 30 min, 1, 2 and 4 hr after administration. The blood was collected in a 1.5 mL tube containing 1% heparin dispensed thereto in advance, and centrifuged (12000 rpm, 10 min, 4° C.) to give plasma. Thereafter, 3% sulfosalicylic acid in the same amount as the plasma was added and blended, and the mixture was stood still on ice for 1 hr and centrifuged (12000 rpm, 10 min, 4° C.) to give deproteinized plasma as a sample for analysis. L-arginine in the sample for analysis was quantified using an automatic amino acid analyzer (JOEL JLC-500/V).

The quantification results of L-arginine (Arg) in the plasma are shown in FIG. 1.

In FIG. 1, a significant increase in the maximum drug concentration ($C_{max}$) and a shortened maximum drug concentration time ($T_{max}$) are observed in group 3 (L-citrulline and L-arginine administration group) at 30 min and 1 hr after administration, as compared to group 1 (L-citrulline administration group) and group 2 (L-arginine administration group).

Furthermore, the area under the blood concentration-time curve (AUC, the area enclosed by blood drug concentration and time) was calculated, which is a useful index for comparison of bioavailability of drugs and the like. The results are shown in Table 1.

TABLE 1

| administration group | AUC (nmol · h/mL) | |
| --- | --- | --- |
| | 0-30 min | 0-1 hr |
| group 1 | 37.1 | 135.6 |
| group 2 | 74.4 | 252.3 |
| group 3 | 162.1 | 449.3 |

As is clear from Table 1, a significant increase in the area under the blood concentration-time curve is observed in group 3 (L-citrulline and L-arginine administration group) within 30 min and within 1 hr after administration, as compared to group 1 (L-citrulline administration group) and group 2 (L-arginine administration group).

Experimental Example 2

14-Week-old male New Zealand rabbits (KITAYAMA LABES Co., Ltd.) were purchased, preliminarily bred for 28 days and divided into 3 groups (n=3 or 4). After fasting for 16 hr, L-citrulline and L-arginine were orally administered to the rabbits of group 1 and group 2, respectively, by a sonde to achieve 2.85 mmol/kg per rabbit for both (499.3 mg/kg and 496.5 mg/kg, respectively). Moreover, L-citrulline and L-arginine were orally administered to the rabbits of group 3 by is a sonde to achieve 1.43 mmol/kg per rabbit (250.5 mg/kg and 249.1 mg/kg, respectively).

The blood was collected from the ear vein before administration, and 30 min, 1, 2 and 4 hr after administration, and subjected to quantification of L-arginine, NO metabolite and cGMP in plasma. The blood was collected in a 1.5 mL tube containing 1% heparin dispensed thereto in advance (for quantification of L-arginine) and a disodium ethylenediaminetetraacetate (EDTA-2Na)-added tube (for quantification of NO metabolite and cGMP), and centrifuged (12000 rpm, 10 min, 4° C.) to give plasma. In heparin plasma thereafter, 3% sulfosalicylic acid in the same amount as the plasma was added and blended, and the mixture was stood still on ice for 1 hr and centrifuged (12000 rpm, 10 min, 4° C.) to give deproteinized plasma as a sample for analysis.

L-arginine in the sample for analysis was quantified using an automatic amino acid analyzer (JOEL JLC-500/V), NO metabolite ($NO_x$:$NO_2$+$NO_3$) was quantified using a nitrogen oxide analyzer (Eicom ENO10), and cGMP was quantified by high performance liquid chromatography (HPLC) (Amersham Pharmacia RPN226).

In addition, at 35 min to 40 min after administration, the blood flow near the ear artery was measured using a laser doppler blood flow analyzer (Laser Doppler Perfusion Imager PIMII). The blood flow was measured at 2 points of 3 cm from the ear artery root and the tip of the artery, and an average was taken. The relative value of each group to the blood flow before administration as 1 was determined and expressed in an amount of increase (Δblood flow) as compared to that before administration.

Figure 2:
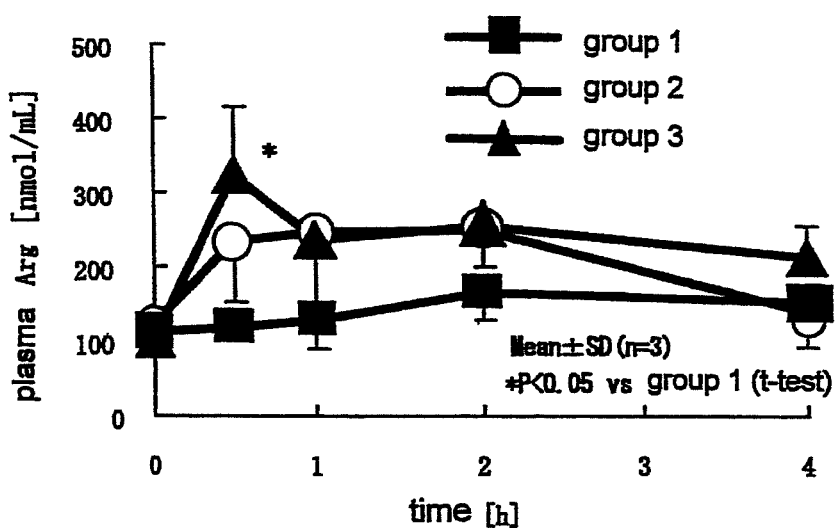
FIG. 2 shows time-course changes in plasma arginine level (unit: nmol/ml) after oral administration.
Figure 3:
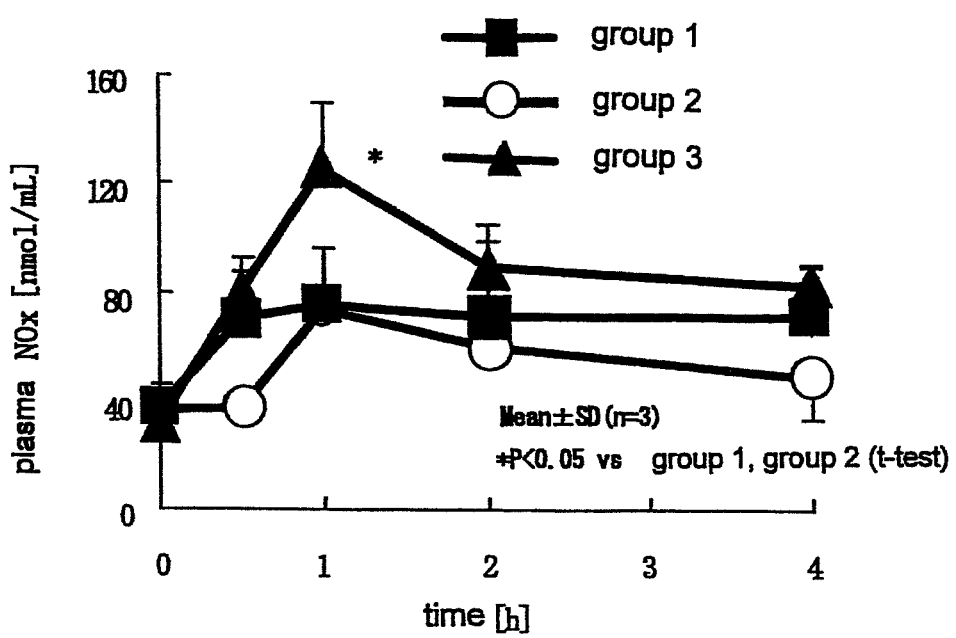
FIG. 3 shows time-course changes in plasma NO metabolite ($NO_x$) level (unit: nmol/mL) after oral administration.
Figure 4:
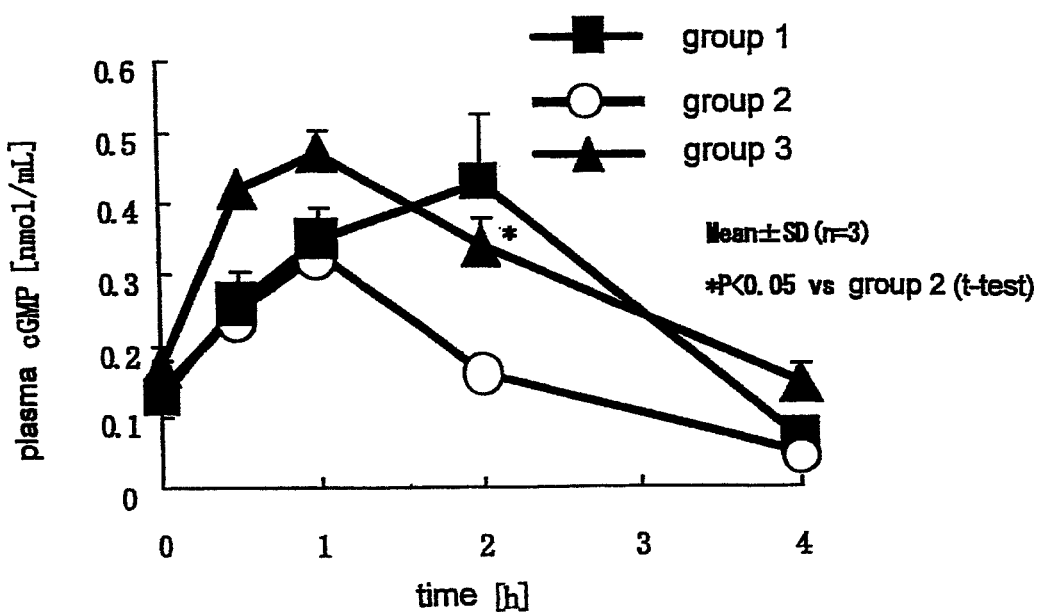
FIG. 4 shows time-course changes in plasma cGMP level (unit: nmol/mL) after oral administration.
Figure 5:
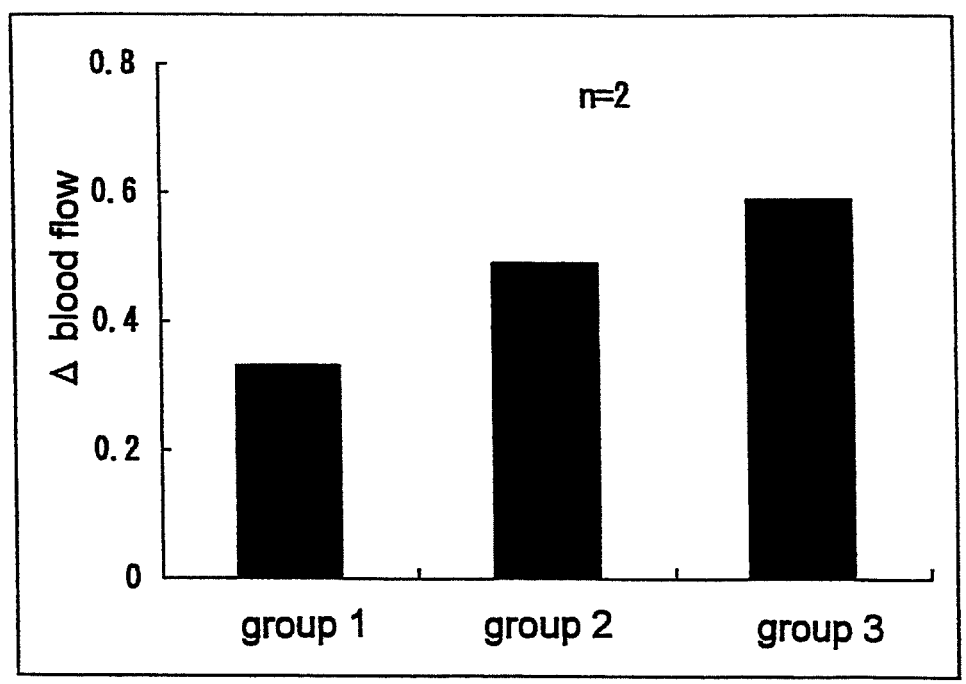
FIG. 5 shows increase in ear artery blood flow 35-40 min after oral administration.

The quantification results of L-arginine (Arg), NO metabolite ($NO_x$) and cGMP in plasma are shown in FIG. 2-FIG. 4, and the measurement results of blood flow are shown in FIG. 5.

As is clear from FIG. 2-FIG. 4, an increase in the maximum drug concentration ($C_{max}$) is observed in all of L-arginine, NO metabolite and cGMP in plasma in group 3 (L-citrulline and L-arginine administration group) at 30 min and 1 hr after administration, as compared to group 1 (L-citrulline administration group) and group 2 (L-arginine administration group). In addition, shortened maximum drug concentration time ($T_{max}$) is observed in L-arginine and cGMP in plasma.

In FIG. 2, the plasma L-arginine level after 0.5 hr of group 3 shows a significant difference of $P<0.05$ from group 1. In FIG. 3, the plasma NO metabolite level after 1 hr of group 3 shows a significant difference of $P<0.05$ from group 1 and group 2. In FIG. 4, the plasma cGMP level of group 3 after 2 hr shows a significant difference of $P<0.05$ from group 2.

As is clear from FIG. 5, the ear artery blood flow of group 3 (L-citrulline and L-arginine administration group) shows an increase as compared to group 1 (L-citrulline administration group) and group 2 (L-arginine administration group). However, since the number is small (n=2), a statistically significant difference is not observed.

Moreover, the area under the blood concentration-time curves of L-arginine, NO metabolite and cGMP in plasma were calculated, and the results are shown in Table 2-Table 4.

TABLE 2

| administration group | AUC (nmol · h/mL) | |
| --- | --- | --- |
| | 0-30 min | 0-1 hr |
| group 1 | 1.7 | 8.1 |
| group 2 | 27.4 | 85.8 |
| group 3 | 55.4 | 144.0 |

TABLE 3

| administration group | AUC (nmol · h/mL) | |
| --- | --- | --- |
| | 0-30 min | 0-1 hr |
| group 1 | 8.1 | 25.7 |
| group 2 | 0.3 | 10.1 |
| group 3 | 12.1 | 47.7 |

TABLE 4

| administration group | AUC (nmol · h/mL) | |
| --- | --- | --- |
| | 0-30 min | 0-1 hr |
| group 1 | 0.033 | 0.12 |
| group 2 | 0.028 | 0.10 |
| group 3 | 0.063 | 0.20 |

As is clear from Table 2-Table 4, group 3 shows an increase in the area under the blood concentration-time curves of all of L-arginine, NO metabolite and cGMP in plasma within 30 min and within 1 hr after administration, as compared to group 1 and group 2.

Examples of the present invention are shown below.

Example 1

Production of Tablet Containing L-Citrulline and L-Arginine

L-Citrulline (68.1 kg), L-arginine (68.1 kg), microcrystalline cellulose (36.0 kg), sucrose fatty acid ester (6.6 kg), calcium phosphate (1.2 kg) and β-cyclodextrin (20.0 kg) are mixed by a conical blender. The obtained mixture is compression molded in a rotary compression molding machine to give tablets.

Example 2

Production of Enteric Tablet Containing L-Citrulline and L-Arginine

The surface of the tablet produced in Example 1 is coated with a shellac solution to give enteric tablets.

Example 3

Production of Enteric Capsule Containing L-Citrulline and L-Arginine

L-Citrulline (68.1 kg), L-arginine (68.1 kg), microcrystalline cellulose (36.0 kg), sucrose fatty acid ester (6.6 kg), calcium phosphate (1.2 kg) and β-cyclodextrin (20.0 kg) are mixed by a conical blender. The obtained mixture (20 kg) and silicon dioxide (0.2 kg) are mixed and stirred. The obtained mixture is fed into a capsule filling machine, and filled in hard capsules to give hard capsules. The surface of the obtained hard capsules is coated with a zein solution to give enteric capsules.

Example 4

Production of Drink Containing L-Citrulline and L-Arginine

L-citrulline (0.64 kg), L-arginine (0.64 kg), erythritol (3 kg), citric acid (0.05 kg), artificial sweetener (3 g) and flavor (0.06 kg) are dissolved in water (50 L, 70° C.) by stirring, and the solution is adjusted to pH 3.3 with citric acid. The mixture is sterilized by plate sterilization and filled in a bottle. Then, the bottle is sterilized by pasteurizer to give drink.

Example 5

Production of Drink Containing L-Citrulline and L-Arginine

L-citrulline (1.00 kg), L-arginine (0.28 kg), erythritol (3 kg), citric acid (0.05 kg), artificial sweetener (3 g) and flavor (0.06 kg) are dissolved in water (50 L, 70° C.) by stirring, and the solution is adjusted to pH 3.3 with citric acid. The mixture is sterilized by plate sterilization and filled in a bottle. Then, the bottle is sterilized by pasteurizer to give drink.

INDUSTRIAL APPLICABILITY

According to the present invention, a rapid-acting, blood arginine level-increasing oral preparation capable of increasing arginine blood level rapidly and effectively can be provided. By ingestion of the oral preparation of the present invention, various symptoms caused by decreased blood flow and increased blood ammonia level can be improved in a short time or effectively prevented.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on a patent application No. 2007-264090 filed in Japan, the contents of which are incorporated in full herein by this reference.

The invention claimed is:

1. A method of increasing blood flow in a subject comprising (i) providing a subject in need of increased blood flow within 1 hour and (ii) administering to the subject (a) citrulline or a salt thereof in an amount of at least 0.88 g at one time and (b) arginine or a salt thereof in an amount of at least 0.87 g at one time, so as to increase the blood flow of the subject within 1 hour after the administration of the citrulline or a salt thereof and arginine or a salt thereof.

2. The method of claim 1, wherein the administered amount of citrulline or a salt thereof is at least 250.5 mg/kg of subject weight, and the administered amount of arginine or a salt thereof is at least 249.1 mg/kg of subject weight.

3. The method of claim 1, wherein the administered amount of citrulline or a salt thereof achieves a concentration of citrulline or a salt thereof in the subject of at least 1.43 mmol/kg of subject weight, and the administered dose of arginine or a salt thereof achieves a concentration of arginine or a salt thereof in the subject of at least 1.43 mmol/kg of subject weight.

4. A method of increasing blood flow in a subject comprising (i) providing a subject in need of increased blood flow within 40 minutes and (ii) administering to the subject (a) citrulline or a salt thereof in an amount of at least 0.88 g at one time and (b) arginine or a salt thereof in an amount of at least 0.87 g at one time, so as to increase the blood flow of the subject within 40 minutes after the administration of the citrulline or a salt thereof and arginine or a salt thereof.

5. The method of claim 4, wherein the administered amount of citrulline or a salt thereof is at least 250.5 mg/kg of subject weight, and the administered amount of arginine or a salt thereof is at least 249.1 mg/kg of subject weight.

6. The method of claim 4, wherein the administered amount of citrulline or a salt thereof achieves a concentration of citrulline or a salt thereof in the subject of at least 1.43 mmol/kg of subject weight, and the administered dose of arginine or a salt thereof achieves a concentration of arginine or a salt thereof in the subject of at least 1.43 mmol/kg of subject weight.

* * * * *